United States Patent [19]
Parker et al.

[11] Patent Number: 5,279,796
[45] Date of Patent: Jan. 18, 1994

[54] DEMOUNTABLE, REPLACEABLE ASPIRATING NEEDLE CARTRIDGE ASSEMBLY

[75] Inventors: Nicholas Parker, Sunrise; Carmelo R. Cambareri, Plantation; Michael A. Krou, Davie, all of Fla.

[73] Assignee: Coulter Corporation, Miami, Fla.

[21] Appl. No.: 28,752

[22] Filed: Mar. 9, 1993

Related U.S. Application Data

[63] Continuation of Ser. No. 717,135, Jun. 18, 1991, abandoned.

[51] Int. Cl.⁵ .............................. B65B 31/06
[52] U.S. Cl. ........................... 422/100; 422/102; 422/103; 422/104; 436/49; 436/54; 436/180; 141/91; 141/97
[58] Field of Search ............. 422/100, 99, 102, 103, 422/104; 436/49, 54, 180; 141/91, 97, 329, 330, 382

[56] References Cited

U.S. PATENT DOCUMENTS

| | | | |
|---|---|---|---|
| 3,340,671 | 9/1967 | Loo | 141/329 |
| 3,788,519 | 1/1974 | Mengel | 141/329 |
| 4,564,054 | 1/1986 | Gustavsson | 141/329 |
| 4,697,624 | 10/1987 | Bower et al. | 141/97 |
| 4,957,706 | 9/1990 | Romette et al. | 422/102 |
| 5,117,875 | 6/1992 | Marrucchi | 141/329 |

OTHER PUBLICATIONS

Coulter® JS—Operator Tips (Manual) PN4235799 (D), Apr. 1992; pp. 1, 2 and 4-9 and 4-10.

*Primary Examiner*—James C. Housel
*Assistant Examiner*—Harold Y. Pyon
*Attorney, Agent, or Firm*—Carl Fissell, Jr.; Gerald R. Hibnick

[57] ABSTRACT

An aspiration apparatus primarily including a biohazard-safe aspirating cartridge assembly for use with material which might be hazardous to humans. The cartridge assembly includes a longitudinally expandable and contractible washing chamber, within which a fluid aspirating needle is longitudinally positioned. Opposite ends of the washing chamber are secured to a pair of telescopically slidable mounting members, which are pluggably mountable to an operably associated support. A locking element surrounds one of the mounting members, for preventing accidental/premature telescoping. Intentional release of the locking element enables the pair of slidable members to be telescoped together by the drive means, causing the washing chamber to contract, permitting the tip of the aspirating needle to be extended out of the chamber, for penetration of an operably associated sealed container of material, for example whole blood.

15 Claims, 3 Drawing Sheets

DEMOUNTABLE, REPLACEABLE ASPIRATING NEEDLE CARTRIDGE ASSEMBLY

This is a continuation of co-pending application Ser. No. 07/717,135, filed on Jun. 18, 1991, now abandoned.

BACKGROUND OF THE INVENTION

This invention relates broadly to fluid handling apparatus and, more specifically, to fluid handling apparatus of the type which is or can be used with fluids which are or can be harmful to humans and/or to fluids which are corrosive, or are bacterially contaminated, or which are otherwise biohazardous for one reason or another.

The handling of hazardous materials, especially hazardous fluid materials, is a worldwide consummate problem. When a human operator is required to become involved in such handling of these materials, the problem is even more severe. Fluid materials, generally, are particularly troublesome due to their capacity for leaking, corroding, spilling, entering the immediate surroundings in aerosol form, etc.

In the biomedical field and particularly in a hospital environment, the requirement for a safe, sanitary and biologically clean working atmosphere is of the highest order and importance. Additionally, each piece of biomedical apparatus must meet the highest and strictest safety and sanitary codes for biohazard containment. The present worldwide problem of infectious disease, such as the HIV virus, places a high burden on the manufacturer of biomedical apparatus, with respect to the chemistry/reagents involved in using the apparatus, as well as with respect to the human operator, who must interface with and work with such apparatus.

A particular area of concern is that of hematology apparatus and specifically automated hematology apparatus which employs freshly venapunctured human blood as a fluid sample material for diagnosis and detection of disease. Most, if not all, human blood used for test and diagnostic purposes is drawn by needle puncture from veins in the human anatomy. The fresh fluid blood is captured in test tube-like containers or vials which are tightly capped with flexible, puncturable caps or stoppers. Such containers are patient-identified (e.g. bar coded) and then transferred to diagnostic centers for diagnostic examination or to temporary cold storage.

At this juncture in the fluid (blood sample) handling routine, there is relatively little concern vis-a-vis biohazard containment, since the blood, should it be hazardous, is completely sealed from the atmosphere as well as from the person of the handler/operator.

The next step in the routine, however, can create the first of many biohazard problems. If the blood-containing test tube or vial is introduced into the testing apparatus with the tube cap in place, there is little danger to the operator. On the other hand, if the operator is required to remove the cap from the test tube or vial and decant the blood into the test apparatus, there could be substantial risk of contamination to the operator and to the adjacent area.

For example, if the human operator is required to perform a microscopic examination of the blood, then a portion of the fluid blood must be placed on a microscope slide, so as to be viewed under a microscope or other optical instrument for examination. This obviously necessitates some handling of the blood out of the tube or vial. In such case, contamination of the operator can occur at any time from a variety of causes. Not the least of these is tube breakage, slide breakage, blood spillage, etc. A search for automation of these steps has been an ongoing medical industry quest for some time.

Many, if not most, modern medical facilities, hospitals and diagnostic laboratories and centers, universally employ automatic diagnostic hematology tools in an effort to eliminate human error, as well as to reduce the required labor force so as to relieve highly skilled and trained technical personnel for more demanding tasks and, in addition, to prevent the possibility of biohazard contamination. Some of these automated hematology devices are more or less biohazard free due to containment devices, which either prevent easy access to the blood during diagnostic routines or avoid human operator intervention with the blood container until the diagnostic routine is completed. Still, there is the ever-present danger from the technician who tries to "help the machine along", or becomes over-anxious for the results and thereby intervenes in the operation prior to its completion or termination. By removing protective shielding from the blood container, he or she thereby exposes himself or herself to the risk of infection or injury from the hazardous contents, if any.

Certain recently introduced hematology equipment utilizes an automatic so-called "cap piercer, washer aspirator", wherein a capped and bar coded sample vial, containing a sample of human blood, is dropped into a sample carrier, which then automatically reads the bar code, introduces an aspirating needle into and through the vial cap, and withdraws a portion of the blood sample, for use in operably associated diagnostic apparatus. The aspirating needle is withdrawn from the blood sample vial, while simultaneously being washed, and finally retracted out of the way, permitting the next sample to be introduced into the sample carrier of the apparatus.

Such apparatus as the foregoing is reasonably effective in preventing biohazard contamination. However, there comes a time in the operation of the apparatus when, either because of a clog of the aspirating needle, or the fact that the aspirating needle has become bent, dulled or broken, it is necessary to remove this element of the combination and replace it with a new aspirating needle. Obviously, without more, the operator must, in most instances, handle the aspirating needle which, could contain hazardous sample material. Should the operator prick a finger or the skin, the hazardous material could be introduced quickly into the bloodstream of the operator, often with serious or tragic results.

SUMMARY OF THE INVENTION

The preferred embodiment of the present invention completely avoids the above mentioned and other operably associated problems by providing a pluggably demountable aspirating needle cartridge, which is completely self-contained and is provided with means that at all times completely shields the aspirating needle from the operator, thus avoiding the main source of contamination from the hazardous material. In addition, the preferred embodiment of the present invention can be fabricated such that the entire aspirating needle cartridge can be considered a "throwaway" item; so that, instead of repairing a damaged needle which may be bent, dulled or broken, or otherwise having to thoroughly clean or repair the needle cartridge assembly, the entire unitary assembly can be thrown away and a fresh needle cartridge introduced into the apparatus.

To this end, the device, as will be described in detail later on herein, is provided with means for demountably, slidably, pluggably inserting the needle cartridge into the operably associated apparatus and thereafter, when the needle cartridge has served its useful purpose or life, the entire cartridge can be slidably dismounted safely and removed from the associated apparatus and disposed in a biohazard safety type container.

DETAILED DESCRIPTION OF THE INVENTION

Figure 1:
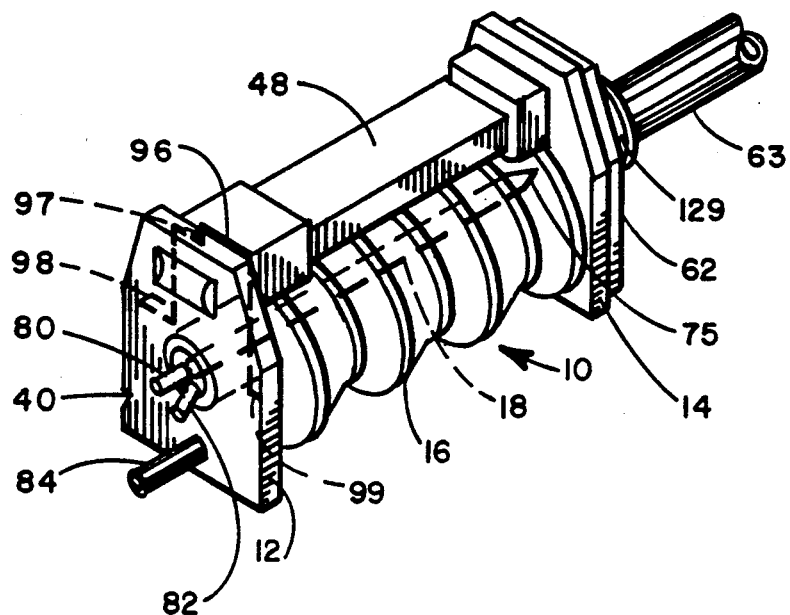
FIG. 1 is a perspective view of the primary components of the needle cartridge assembly.

The aspirating needle cartridge assembly of the present invention is illustrated most clearly in the perspective view of FIG. 1. As shown, the device comprises four major subassemblies which together form a biohazard-free, demountable, pluggable, fluid handling aspirating needle cartridge, which can be mounted to and dismounted from a supporting structure (FIG. 2) attached to operably associated hematology or other test apparatus.

The fluid handling biohazard-free, aspirating needle cartridge assembly 10 includes a lower support or base 12, an upper support or top 14, a flexible, compressible, washing chamber 16, and an aspirating member or needle 18. The assembled fluid handling and aspirating needle cartridge 10 is adapted to be slidably attached to a rigid supporting structure 20, illustrated in FIG. 2. The supporting structure 20 is fastened, as by bolts 22, to an associated hematology apparatus (not shown), with which the cartridge assembly is to be employed.

Figure 3:
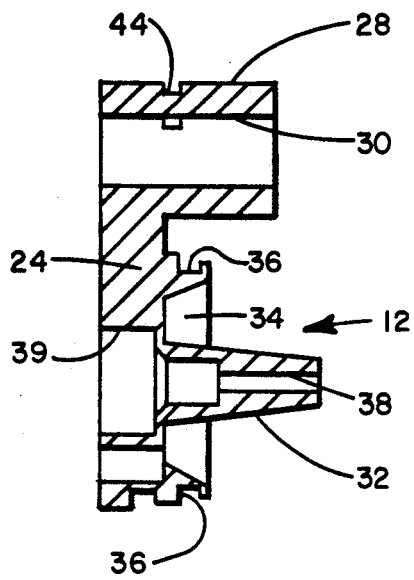
FIG. 3 is a sectional view along the line 3—3 of FIG. 4 of the lower support or base of the cartridge assembly.
Figure 4:
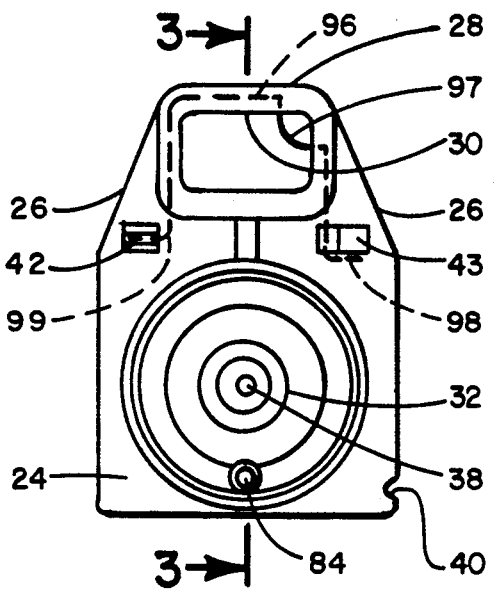
FIG. 4 is a plan view of the lower support of FIG. 3.

The lower support or base 12 is shown in FIGS. 3 and 4 to comprise a substantially rectangular member 24 having angular edge portions 26 (FIG. 4). An integral, upstanding, rectangularly shaped, stub pedestal 28 projects from the member 24 adjacent the edges 26. A rectangular opening or bore 30 extends completely through the pedestal 28. A central, circular, truncated, pyramidal member 32 (FIG. 3) projects from the central area of the member 24. A shallow, circular recess 34 is provided around the pyramidal member 32. A circular groove 36 encircles the rim of the member 32. A stepped, circular opening or bore 38 extends completely through the pyramidal member 32 and at one end defines a recessed seat 39. One edge of the member 24 has a small indent or notch 40 (FIG. 4) cut therein. Two vertical clip retainers 42 and 43 (FIG. 4) are located adjacent to each of the angular edges 26. The pedestal 28 has a continuous groove 44 surrounding three sides thereof.

Figure 5:
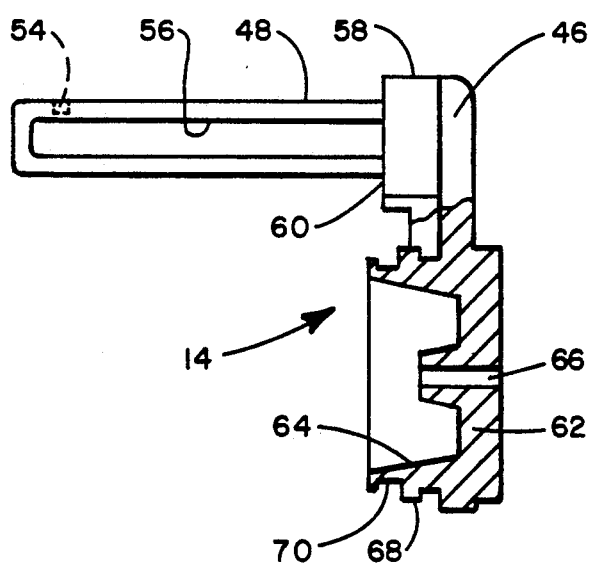
FIG. 5 is a partial sectional view along the line 5—5 of FIG. 6 of the upper support or top of the cartridge assembly.
Figure 6:
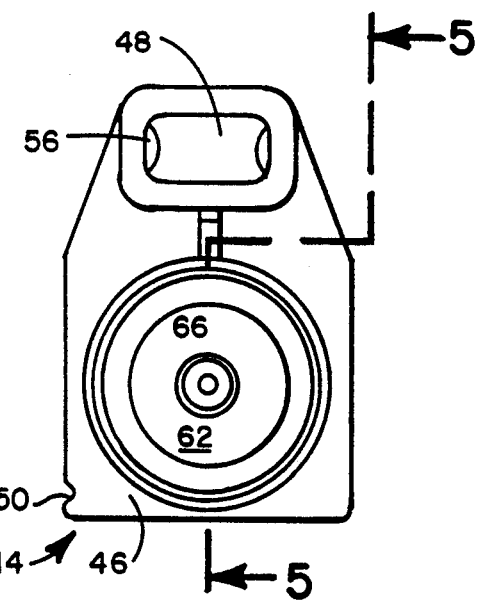
FIG. 6 is a plan view of the upper support of FIG. 5.

The upper support or top 14 of the aspirating needle cartridge 10 is seen in FIGS. 5 and 6 to comprise a substantially rectangular member 46, provided with an integral, depending, elongated, rectangular post or pillar 48. One edge of the member 46 is provided with a notch or indent 50 similar to the notch 40 in the member 24. The external end portion of the pillar 48 includes angular notches 54 on opposite edge portions (FIG. 5). Two shallow, weight relief grooves 56 extend longitudinally along opposite sides of the pillar 48. The pillar 48 terminates at a root end 58 in a ledge 60. The central, upper portion of the member 46 includes an integral, upstanding, circular projection 62, which will support the capped end of the test tube or vial 63 containing sample fluid to be aspirated. The lower portion of the member 46 is provided with a shallow, circular trough 64 (FIG. 5) with a small, central, opening or bore 66 extending therethrough. The member 46 has an outer rim or edge 68, which is undercut to provide a shallow, circular groove 70, similar to the groove 36 in the lower support member 12.

Figure 7:
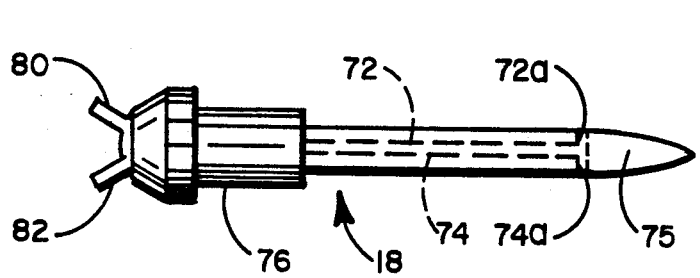
FIG. 7 is a side elevational view of the aspirating needle.
Figure 8:
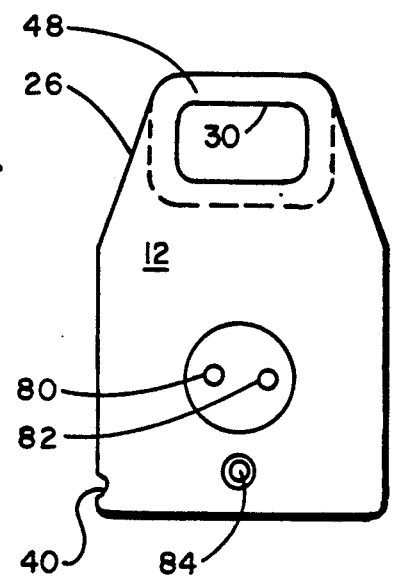
FIG. 8 is a plan view of the bottom of the apparatus of FIG. 1, showing the orientation of the needle aspirating apertures.

The aspirating member or needle 18, as shown in FIG. 7, is double walled and includes two separate and independent parallel channels 72 and 74 extending longitudinally, with each channel terminating near the cap piercing end 75 in a separate inlet/outlet opening 72a and 74a, respectively. The needle 18 is of material, for example stainless steel, unaffected by the blood, chemistry/reagents with which it is to be employed. The base 76 of the needle 18 is configured to be fixed within the seat 39 of the bore 38 in the base support 12 (FIG. 3); or the base 76 can be molded into the support 12 The base 76 includes two fluid connectors 80 and 82 which are connected with channels 72 and 74, respectively. A third connector 84, shown in FIG. 8, is a waste outlet connector.

Figure 9:
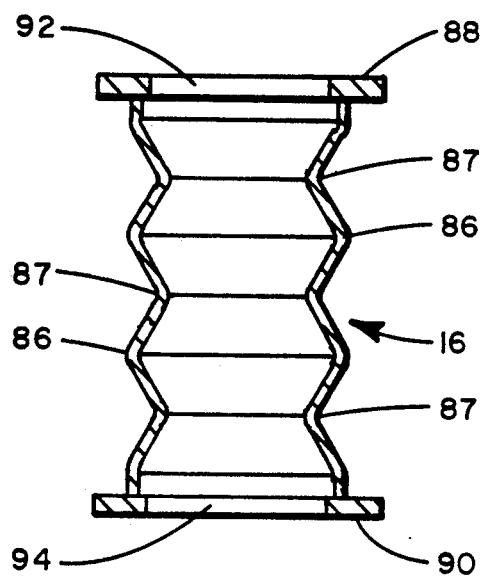
FIG. 9 is a sectional, side elevational view of the flexible washing chamber.

FIG. 9, illustrates, in sectional side elevation the flexible, compressible washing chamber 16. The washing chamber 16 is of material which is substantially impervious and inert to the blood, chemistry/reagents with which it is to be used. Such material can be plastic from the family of plastics known as silicon rubber. The washing chamber 16 is constructed as a bellows, which is circumferentially semi-rigid or rigid enough to be self-supporting and is longitudinally compressible, but sufficiently resilient to spring back to its original longitudinal, uncompressed condition and form after being compressed. The washing chamber 16, includes alternating, ring-like portions 86 and compression folds 87, enabling the chamber 16 to be compressed and then returned to its original, extended condition, when the compression means are released or relieved.

The top and bottom edges 88 and 90, respectively, of the washing chamber 16, are integral, circular collars or rings 92 and 94, which retain and immobilize the chamber 16 within the members 24 and 46, in the grooves 36 and 70.

Figure 10:
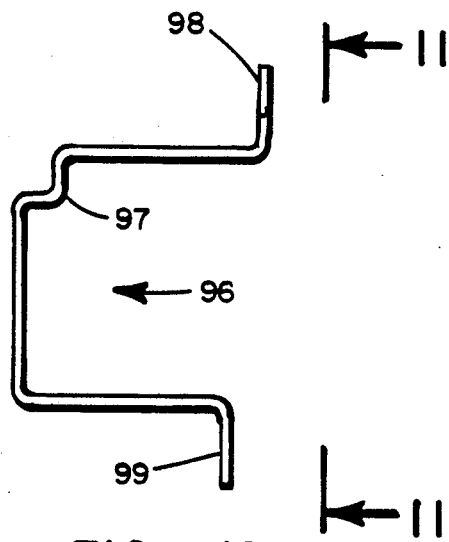
FIGS. 10 and 11 are detail views of the safety lock retaining clip, as used with the cartridge assembly.
Figure 11:
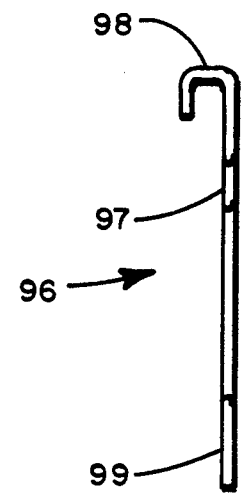

An elongated, irregularly shaped, safety retaining clip 96, illustrated in FIG. 10, includes a detent elbow 97, a hook-like end 98, shown in FIG. 11, and the other end is part 99. The retaining clip 96 acts to retain the upper support or top 14 in non-slidable, fixed relationship relative to the lower support or base 12.

Figure 2:
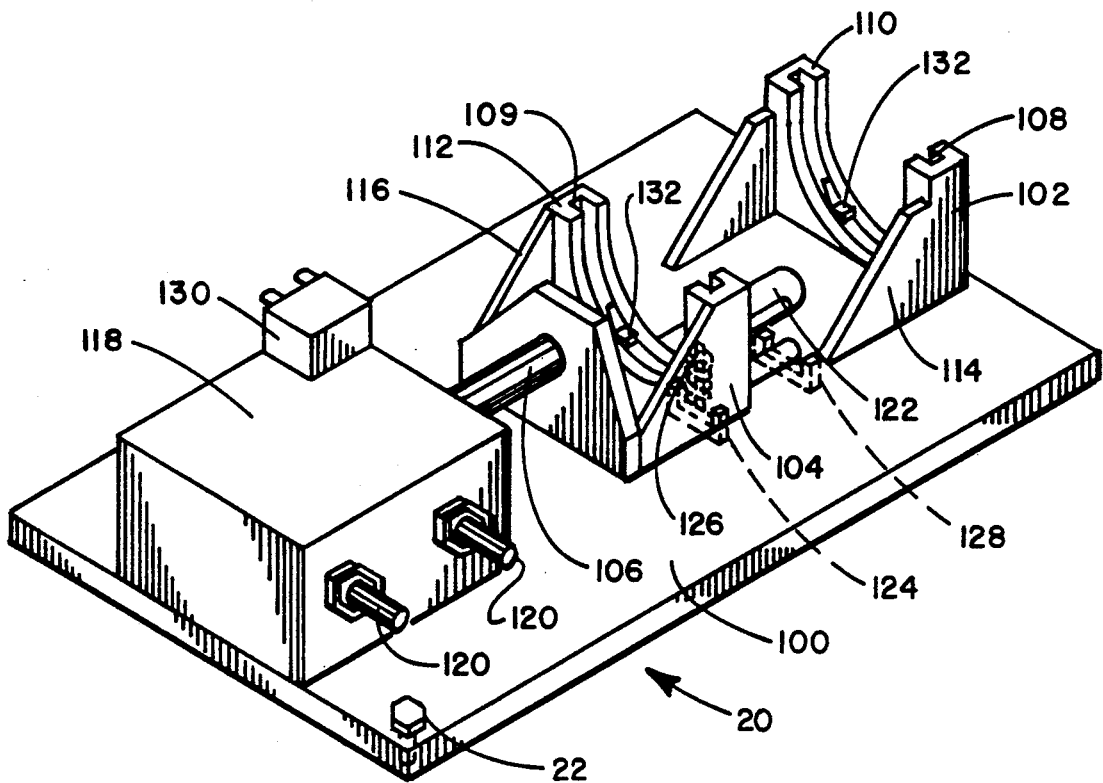
FIG. 2 is a perspective view of the supporting structure of the assembly.

The cartridge 10 is supported on a operably associated system (not shown) by means of the supporting structure 20 shown in FIG. 2. The supporting structure 20 comprises a rigid, flat, rectangular, plate-like member 100, on which is mounted a front support member or shelf 102. A rear support member or shelf 104 is mounted on a movable drive rod 106. Each supporting shelf 102 and 104 has an oppositely disposed, parallel, shallow groove 108, 109 extending inwardly from the open end 110, 112 of each shelf 102, 104. Each shelf is provided with rigidifying gussets 114 and 116, respectively.

Drive means, for extending the aspirating needle 18 into and retracting it from the fluid sample (blood) supply vial 63, can comprise a drive mechanism 118, which, if pneumatic, can be energized over pneumatic input/output connectors 120, from a suitable source of compressed air (not shown). The movable, slidable drive rod 106 extends out of the drive mechanism 118 and is secured to the rear shelf 104 to permit the shelf to be slidably movable reciprocally in a mating guide slot 122 in the plate-like member 100.

The cartridge 10 is assembled by first introducing the needle 18 into the guide opening or bore 38 in the base 12 (FIG. 3). Adhesive or other means can be used to fix the needle 18 in position within the base 12 or the needle 18 can be molded in place. The needle 18 is oriented as in FIG. 7. The washing chamber 16 then is placed over the needle 18, so that the lower or bottom edge 90 of the chamber 16 encircles the pyramidal member 32, so that the bottom ring 94 of the member 16 is seated within the shallow circular retaining groove 36 in the base 12. The inside diameter of the bottom ring 94 is slightly smaller than the diameter of the groove 36, producing a relatively tight fit between the groove 36 and the ring 94. Next, the washing chamber 16 and the base 12 are to be assembled to the upper support 14 (FIG. 1).

The retaining clip 96 is inserted into the groove 44 (FIG. 4) in the stub pedestal 28, so that the ends 98 and 99 of the clip 96 are entrapped by the clip retainers 43 and 42. The end 99 of the retainer clip is pressed into a slotted open top of the clip retainer 42. The hooked end 98 is pressed under the edge of the clip retainer 43. The post 48 then is inserted within the rectangular open bore 30 of the pedestal 28. Next, the end 98 of the clip 96 is pushed toward the bore 30, so that the post 48 slides freely in the bore 30, but the retaining clip 96 snaps in to the notch 54 of the post, so the tip 75 of the needle 18 projects into the central bore 66 in the projection 62 of the member 46 and thereby is completely secured. The top ring 92 of the washing chamber 16 then is firmly seated in the groove 70 in the rim 68 of the upper support 14. The bellows washing chamber 16 now is substantially secured to the respective supports 12 and 14. The retaining clip 96 is wrapped around the post 48, such that its detent elbow 97 locks with the notch 54 in the post 48. The retaining clip 96, with the notch 54, rigidify the cartridge, locking the upper and lower support members 14 and 12 together and preventing the two from sliding or telescoping relative to each other during handling of the cartridge, so the needle is firmly secured inside the chamber 16.

It should be readily apparent from the foregoing description that the post 48 can be used as a handle member for inserting and removing the cartridge 10 from the supporting structure 20. When the cartridge 10 is completely inserted within the supporting structure 20, the hook-like end 98 of the retaining clip 96 touches the open end 112 of the rear shelf 104, so that the detent 97 of the clip 96 is forced out of the notch 54. In this orientation, the pillar 48 is permitted to slide freely within the bore 30, enabling the sample vial piercing cycle to take place. However, removal of the cartridge 10 from the supporting structure 20 reengages the retaining clip 96 within the notch 54, due to the spring tension on the retaining clip 96, so the needle is again firmly secured safely within the washing chamber.

A plurality of sensor devices can be used for ascertaining the condition and the position of the cartridge 10 within the supporting structure 20. As shown in FIG. 2, in the lower part of the rear shelf 104, a cartridge insertion sensor 124 is engaged by a spring loaded pin 126. The pin 126 is moved inwardly and outwardly as the cartridge 10 is inserted into and removed from the supporting structure 20. An electric signal from the sensor 124, when the pin is in its inward position, indicates that the cartridge 10 is in place and that the sampling/testing operation may be enabled.

Also mounted within the supporting structure 20, forward of the rear shelf, is an aspirating needle insertion sensor 128, which provides automatic means for indicating that the needle 18 has penetrated the closure member 129 of the fluid container 63. A source of vacuum 130 is connected to the needle inlet connector 82, for causing fluid to be withdrawn through needle 18.

The external edge notches 40 and 50, shown in FIGS. 4 and 6, insure that the cartridge is snap-fitted into the front and rear support grooves 108 and 109, by having the notches engage projecting tabs or tangs 132 (FIG. 2) at the lower end of the grooves. Finger or handling pressure, during withdrawal of the cartridge apparatus from the support 20, is sufficient to release the cartridge 10 for this removal.

It now should be appreciated that, during the engagement of the detent 97 of the spring retaining clip 96 in the notch 54 of the post 48, the two portions 12 and 14 of the cartridge 10 cannot be separated upon removal of the cartridge from the supporting structure 20. Thus, since the needle 18 is retained within the bore 38, and well below the top of the bore 66, the needle and especially its tip 75 is never exposed to the human operator and therefore there is no biohazard risk, for example, of scratching or pricking the skin, as might be the case if the needle were to become exposed.

However, should it become necessary to remove the needle 18, this is accomplished easily by pushing the hook-like end 98 of the retaining clip 96 toward the bore 30. The upper and lower supports 14 and 12 then can be separated and the needle 18 becomes accessible.

Another important feature of the preferred embodiment is that, since the needle 18 is retained constantly within the bore 66 in the upper support 14, the needle 18 is coaxially aligned with the fluid sample container 63 which is to be supported and secured against upper flat surface of circular projection 62 (FIG. 6).

Although a specific embodiment has been illustrated and described, it should be obvious to those skilled in the art that certain changes and modifications can be made therein without departing from the invention in its broader aspects, and, therefore, the aim in the appended claims is to cover all such changes and modifications as fall within the true spirit and scope of the invention.

What is claimed is:

1. Apparatus having aspirating means for aspirating fluid material from a supply thereof, said apparatus being constructed and arranged for maintaining said aspirating means in a closed, non-ambient, biohazard-free and contamination-free condition, said apparatus further comprising:
   a) a fluid entry tip at one end of said aspirating means;
   b) drive means connected to said aspirating means for extending said aspirating means into and retracting said aspirating means from the supply of fluid material and thereby defining extended and retracted positions;
   c) a washing chamber enveloping said aspirating means, said washing chamber being flexible and constructed and arranged to be compressed in one position and expanded in the other position;
   d) mounting means for supporting said washing chamber such that said aspirating means is completely enclosed within said washing chamber; and
   e) locking means engaging said washing chamber mounting means for locking said washing chamber in said expanded position.

2. Apparatus according to claim 1, wherein said washing chamber comprises a circumferentially semi-rigid, longitudinally flexible, hollow member surrounding and extending longitudinally of said aspirating means.

3. Apparatus according to claim 1, wherein said aspirating means comprises an elongated, hollow, double walled needle which is longitudinally slidable within said washing chamber, except when said locking means locks said washing chamber in said expanded position.

4. Apparatus according to claim 1, wherein said aspirating means includes support means for supporting the supply of fluid material proximate to and aligned with said fluid entry tip.

5. Apparatus according to claim 1, further including sensor means for sensing said retracted position and said extended position of said aspirating means, thereby indicating when said aspirating means is an operative position, so that fluid material can be withdrawn from the supply thereof by said aspirating means.

6. Apparatus according to claim 1, wherein said mounting means is disposed at opposite ends of said washing chamber such that, in the retracted position of said aspirating means, said aspirating means is completely and safely enclosed by said washing chamber and, in said extended position, said aspirating means fluid entry tip is extended out of said washing chamber for entry into the supply of fluid material and said washing chamber then is compressed by said drive means.

7. Apparatus according to claim 1, wherein said washing chamber comprises a bellows member having opposite ends, said mounting means is attached to said opposite ends of said bellows member, and said mounting means has means defining an aperture at one end thereof through which said fluid entry tip of said aspirating means can be extended into and be retracted from the supply of fluid material.

8. Apparatus according to claim 7, in which said mounting means includes central support means, said aspirating means is secured to said central support means and thereby is aligned with said aperture, thus avoiding possible damage to said fluid entry tip when said aspirating means is driven between said extended and retracted positions.

9. Apparatus according to claim 1, wherein said mounting means for supporting said washing chamber includes a first member disposed at one end of said washing chamber and a second member disposed at the opposite end of said washing chamber; and wherein said first member is telescopically, slidable within said second member, to move said washing chamber from said retracted position to said extended position for extending said aspirating means fluid entry tip out from said washing chamber.

10. Apparatus according to claim 9, wherein said locking means is constructed and arranged for enabling and disabling the telescopically slidable movement of said first member relative to said second member, thus positively preventing said aspirating means and said fluid entry tip from accidentally attaining said extended position.

11. Apparatus according to claim 10, in which said aspirating means is pluggably demountable from an operably associated apparatus and said locking means is constructed and arranged for automatically disabling said telescopically slidable movement when said aspirating means is demounted from the operably associated apparatus.

12. Apparatus according to claim 1, wherein said aspirating means comprises a cartridge assembly, and said mounting means is constructed and arranged for attaching said cartridge assembly to other operably associated apparatus.

13. Apparatus according to claim 12, wherein said cartridge assembly mounting means is configured for slidable, pluggable reception within complementary structural means of the operably associated apparatus.

14. Apparatus according to claim 12, further including sensor means for sensing if said cartridge assembly has been received within the complementary structural means of the operably associated apparatus.

15. Apparatus according to claim 12, wherein said washing chamber mounting means includes means for temporarily latching said cartridge assembly to the operably associated apparatus.

* * * * *